United States Patent
Wing et al.

(10) Patent No.: US 6,447,451 B1
(45) Date of Patent: Sep. 10, 2002

(54) MOBILE ULTRASOUND DIAGNOSTIC INSTRUMENT AND DOCKING STAND

(75) Inventors: Gregory Wing, Carnation; Steven Bunce, Sedro Wooly; Andrew T. Dunn, Redmond; Brian Epps, Seattle; Paul Stevens, Kirkland, all of WA (US)

(73) Assignee: SonoSite, Inc., Bothell, WA (US)

( * ) Notice: Subject to any disclaimer, the term of this patent is extended or adjusted under 35 U.S.C. 154(b) by 0 days.

(21) Appl. No.: 09/564,600

(22) Filed: May 3, 2000

Related U.S. Application Data

(60) Provisional application No. 60/132,515, filed on May 4, 1999.

(51) Int. Cl.⁷ .................................................. A61B 8/01
(52) U.S. Cl. ..................................................... 600/437
(58) Field of Search ...................... 248/289.11; 600/137, 600/104, 102, 106, 437, 459, 228–229; 439/374; 73/618; 128/903, 904

(56) References Cited

U.S. PATENT DOCUMENTS

| | | | |
|---|---|---|---|
| 5,640,960 A | | 6/1997 | Jones et al. ............. 128/661.07 |
| 5,655,741 A | * | 8/1997 | Watkins ................. 248/289.11 |
| 5,687,717 A | | 11/1997 | Halpern et al. ............. 128/630 |
| 5,840,012 A | * | 11/1998 | Krauter et al. .............. 600/102 |
| 5,888,087 A | * | 3/1999 | Hanson et al. .............. 439/374 |

* cited by examiner

Primary Examiner—Marvin M. Lateef
Assistant Examiner—Ruby Jain
(74) Attorney, Agent, or Firm—Townsend and Townsend and Crew LLP; Henry K. Woodward

(57) ABSTRACT

A mobile ultrasound diagnostic instrument including a self-powered ultrasound console having electronics for driving a transducer array and processing reflected ultrasound waves, and a visual display for processed ultrasound waves. A docking stand is provided for the console and includes a sleeve for slidably receiving the console of the instrument, the sleeve being configured to expose the visual display and manual controls of the console. A vertical support positions the sleeve in a raised position above the base, which preferably includes wheels for moving the docking stand and diagnostic instrument during use. The sleeve preferably includes a signal connector for mating with a connector of the console and receiving video signals for auxiliary display. A power connector can be provided for mating with a power connector of the console for operating the console and for charging batteries in the console. The sleeve is attached to the vertical support by universal motion joint whereby the sleeve can be rotated and tilted during use, and the vertical support is extendible to vary height of the sleeve. Preferably the vertical support includes a coupler for joining the first portion of the vertical support attached to the sleeve and a second portion of the vertical support attached to the base, the first portion being removable from the second portion and attachable to a second vertical support such as an immobile stand for desk use.

14 Claims, 6 Drawing Sheets

MOBILE ULTRASOUND DIAGNOSTIC INSTRUMENT AND DOCKING STAND

This application claims the benefit of provisional application 60/132,515 filed May 4, 1999.

BACKGROUND OF THE INVENTION

This invention relates generally to medical ultrasonic diagnostic systems, and more particularly the invention relates to a mobile ultrasound diagnostic instrument and docking stand.

Modem ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc. were smaller desk top units about the size of a personal computer. However, such instruments lack many of the advanced features of today's premium ultrasound systems such as color Doppler imaging and three dimensional display capabilities. As ultrasound systems become more sophisticated they also become bulkier.

Disclosed in U.S. Pat. No. 5,722,412 is a diagnostic ultrasound instrument which exhibits many of the features of a premium ultrasound system in a hand-held unit. The instrument can be produced as a single unit or in a preferred embodiment the instrument is a two-part unit one including a transducer, beamformer, and image processor and the other including a display and power source for both units. In such a configuration the transducer/processor unit can be manipulated with one hand with a cable between the two units enables the video to be shown on the display unit while the lateral unit is held or positioned for optimal viewing of the ultrasound image. The cable also provides energy for the transducer/processor unit from the display unit.

The present invention is directed to a mobile ultrasound diagnostic instrument such as disclosed in the '412 patent and a docking stand which facilitates independent use of the instrument for diagnostic purposes or use of the instrument with larger, more complex systems.

SUMMARY OF THE INVENTION

In accordance with a preferred embodiment of the invention, a mobile ultrasound diagnostic instrument includes a docking stand for a self-powered ultrasound console. The console includes electronics for driving a transducer array and processing reflected ultrasound waves, and a visual display for processed ultrasound waves. The docking stand includes a sleeve for slidably receiving the console of the instrument, the sleeve being configured to expose the visual display and manual controls of the console. A vertical support positions the sleeve in a raised position above a base for the vertical support. In alternative embodiments, controls can be provided in the stand, and the console can comprise a personal computer, for example.

In accordance with features of the invention, the sleeve can include a signal connector for mating with a connector of the console and receiving video signals for auxiliary display. The sleeve can further include a power connector for mating with a power connector of the console for operating the console and for charging batteries in the console. The connector can provide input/output signals.

In accordance with the preferred embodiment, the sleeve is attached to the vertical support by a universal motion joint whereby the sleeve can be rotated and tilted during use or limited incline or rotation only can be provided. The vertical support is extendible to vary the height of the sleeve, and the vertical support can include a coupler for joining a first portion of the vertical support attached to the sleeve and a second portion of the vertical support attached to the base, the first portion being removable from the second portion and attachable to a second vertical support for desk use, for example. The base for the vertical support preferably includes wheels for moving the docking stand, the second vertical support for desk use preferably including an immobile base.

In accordance with other features of the docking stand, an arm can be attached to the vertical support and configured to receive a plurality of ultrasound transducers and cables for use in connecting the scanners and the console. A shelf can be attached to the vertical support for supporting a recorder, for example, and the sleeve can include a recess for receiving gel for use in coupling the transducer array and a human patient.

The invention and objects and features thereof will be more readily apparent from the following detailed description and appended claims when taken with the drawings.

DETAILED DESCRIPTION OF ILLUSTRATIVE EMBODIMENTS

Figure 1:
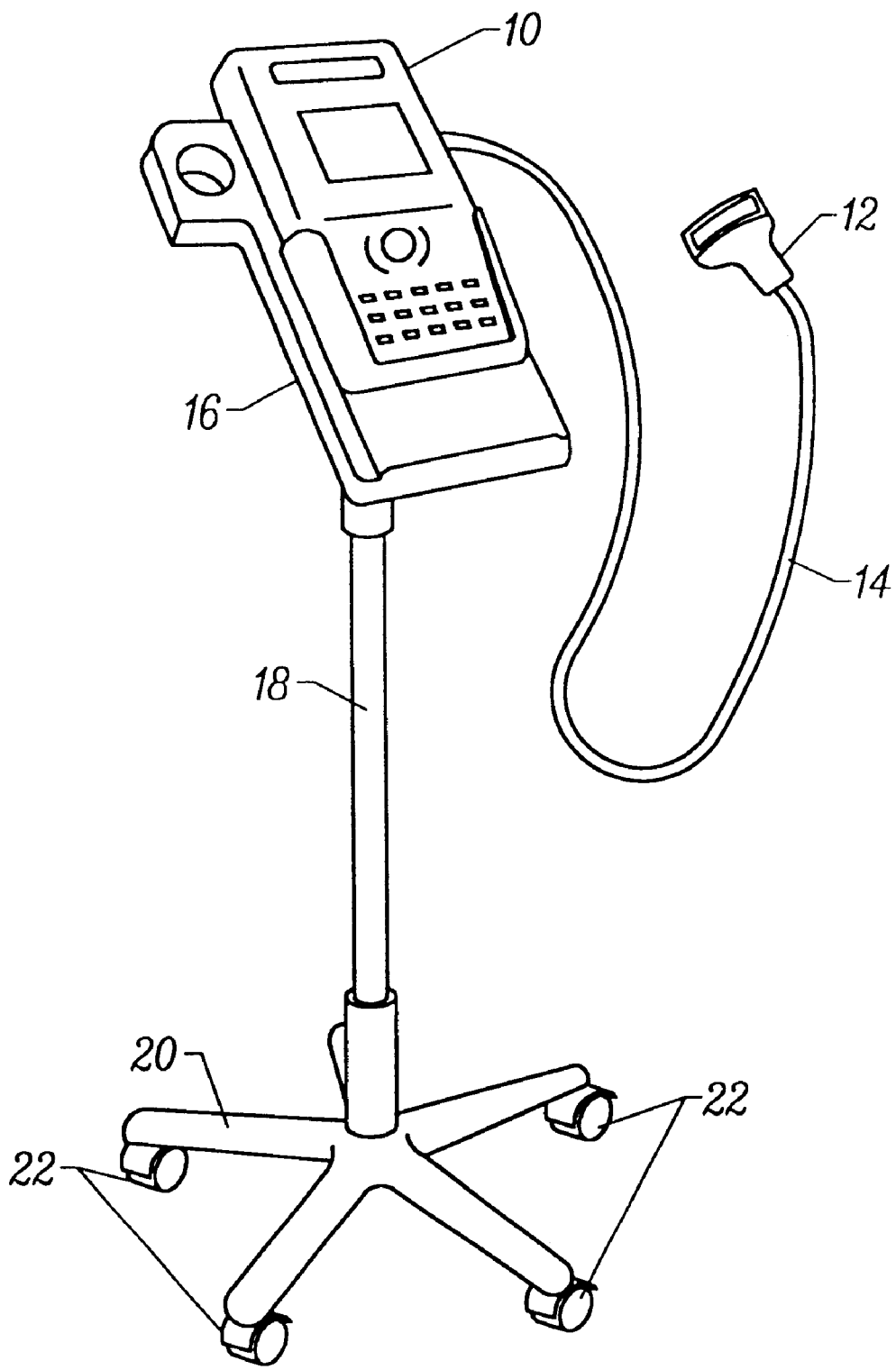
FIG. 1 is a perspective view of an ultrasound diagnostic instrument and docking stand in accordance with one embodiment of the invention.

FIG. 1 is a perspective view of a mobile ultrasound diagnostic instrument and docking stand in accordance with an embodiment of the invention. The diagnostic instrument includes a console 10 and a transducer scanhead 12 which is connected to console 10 through cable 14. The instrument can be of the type disclosed in U.S. Pat. No. 5,722,412.

Figure 2:
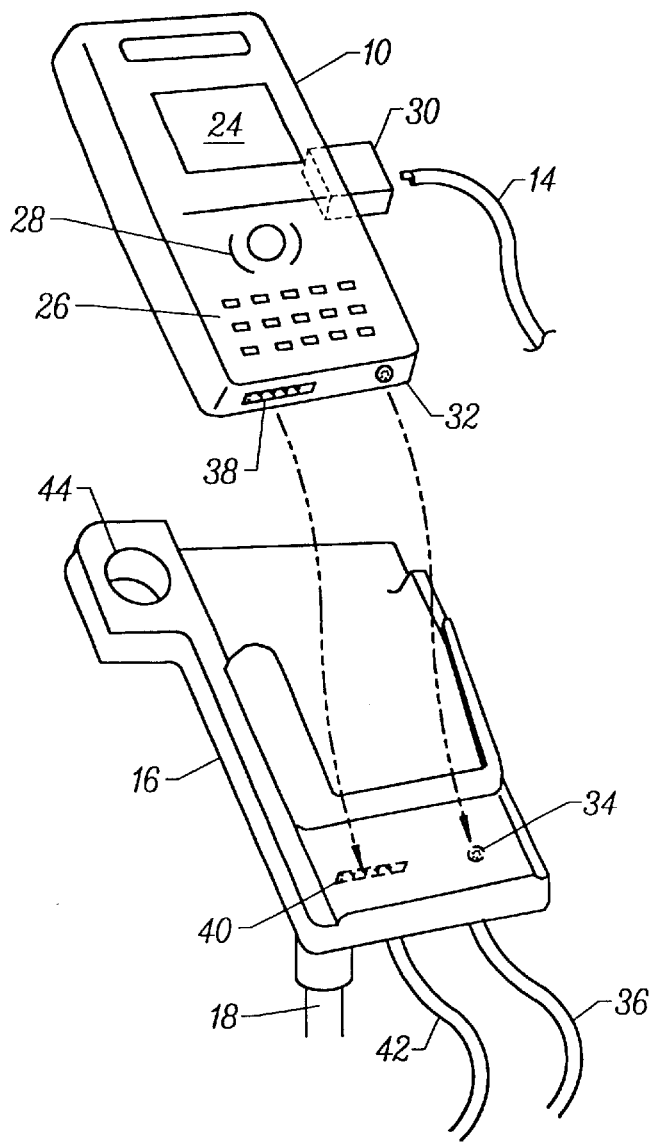
FIG. 2 is an exploded perspective view of a console of the diagnostic instrument and a receptive sleeve of the docking stand.

Console 10 is received within a sleeve receptacle 16 which is supported in a raised position by means of a vertical support 18 that mounts to a base 20 having a plurality of wheels 22 for movement. FIG. 2 is an exploded perspective of console 10 and sleeve 16 which is configured to expose a visual display 24 and manual controls shown generally at 26 and a track ball controller 28 on the console. Cable 14 which connects the scanhead 12 to console 10 includes an adapter 30 which plugs into console 10. Connector 30 allows any one of a plurality of scanheads designed for specific applications to be interfaced with the console, as desired.

Figure 2A:
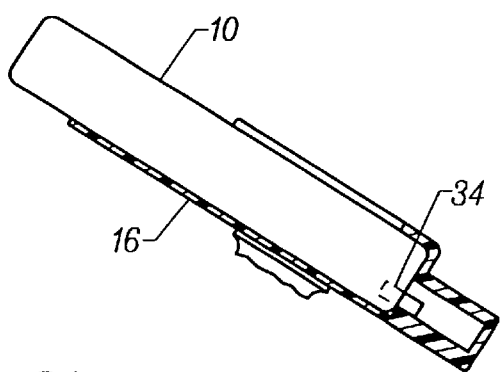
FIG. 2A is a side view in section illustrating the console in the sleeve.

When console 10 is inserted in sleeve 16 as illustrated in the side view of FIG. 2A, a power connector 32 on the base of the console 10 mates with a power connector 34 in the base of the sleeve which connects console 10 to a power supply through power cable 36 for operating the console and for charging batteries in the console. Similarly, a connector 38 in the base of console 10 mates with a connector 40 in the base of sleeve 16 whereby processed signals such as video signals can be connected through cable 42 to an auxiliary display for viewing. The connector can provide input/output signals including serial data and Ethernet/USB, for example. Sleeve 16 includes a receptacle 44 for auxiliary supplies such as a gel for application to a patent prior to ultrasound scanning.

Figure 3:
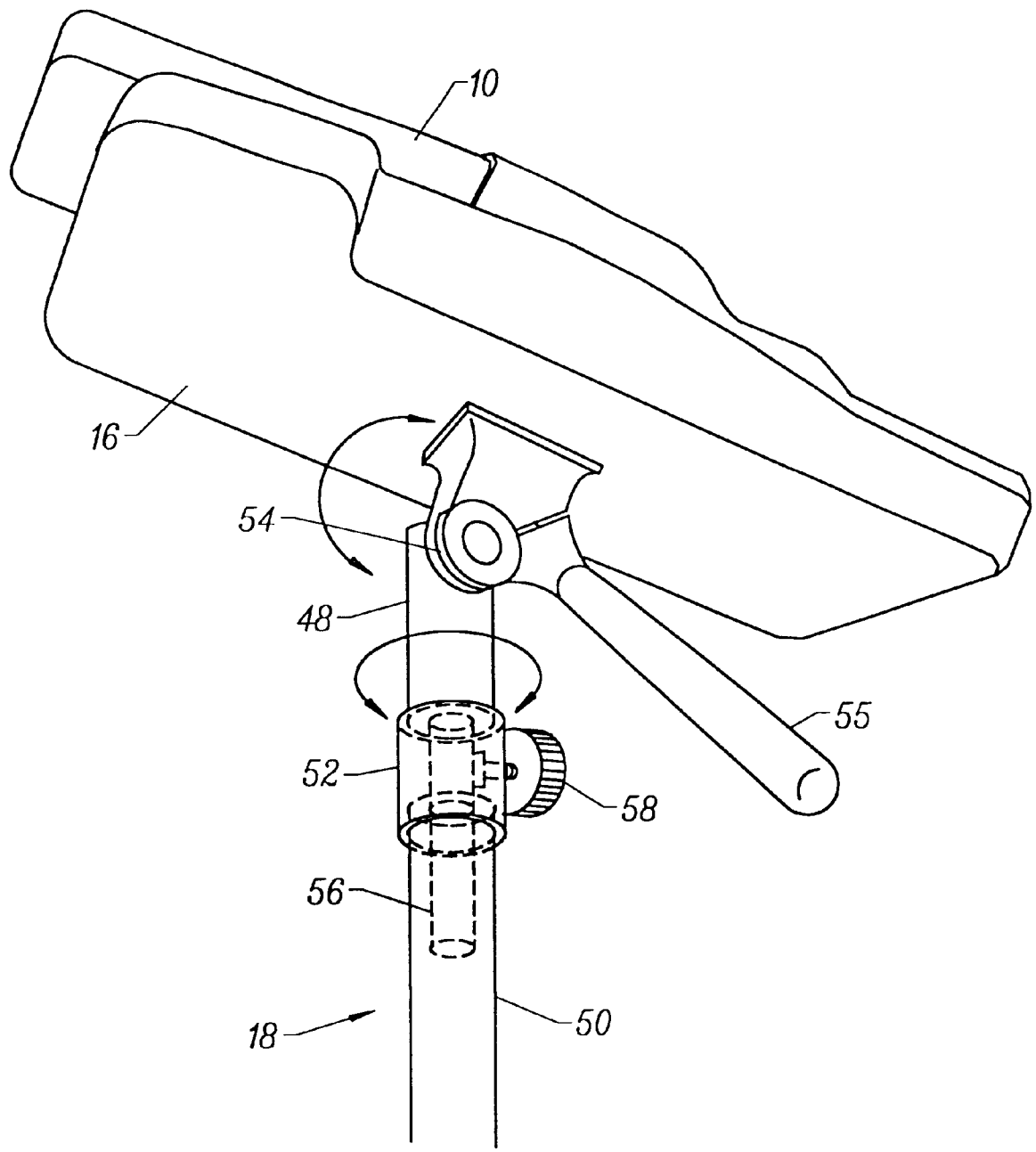
FIG. 3 is a perspective view illustrating universal motion connection of the sleeve and a vertical support of the docking stand.

Referring to FIG. 3, in a preferred embodiment vertical support 18 includes a first portion 48 which mates with a second portion 50 through a coupler shown generally at 52. A coupler 54 attaches sleeve 16 to the first portion 48 whereby sleeve 16 can be tilted at various angles by means of handle 55. Coupler 52 permits rotation of sleeve 16 and the upper portion 48 of the vertical support in a horizontal plane whereby coupler 52 and coupler 54 permit a universal motion joint in positioning the console 10 during use. Upper vertical support 48 includes a depending portion 56 of reduced diameter which is received within the lower vertical support 50 whereby the upper portion 48 is adjustable in height by means of a thumb screw 58. Thus sleeve 16 and console 10 can be varied in height by adjusting depending member 56 with thumb screw 58.

Figure 4:
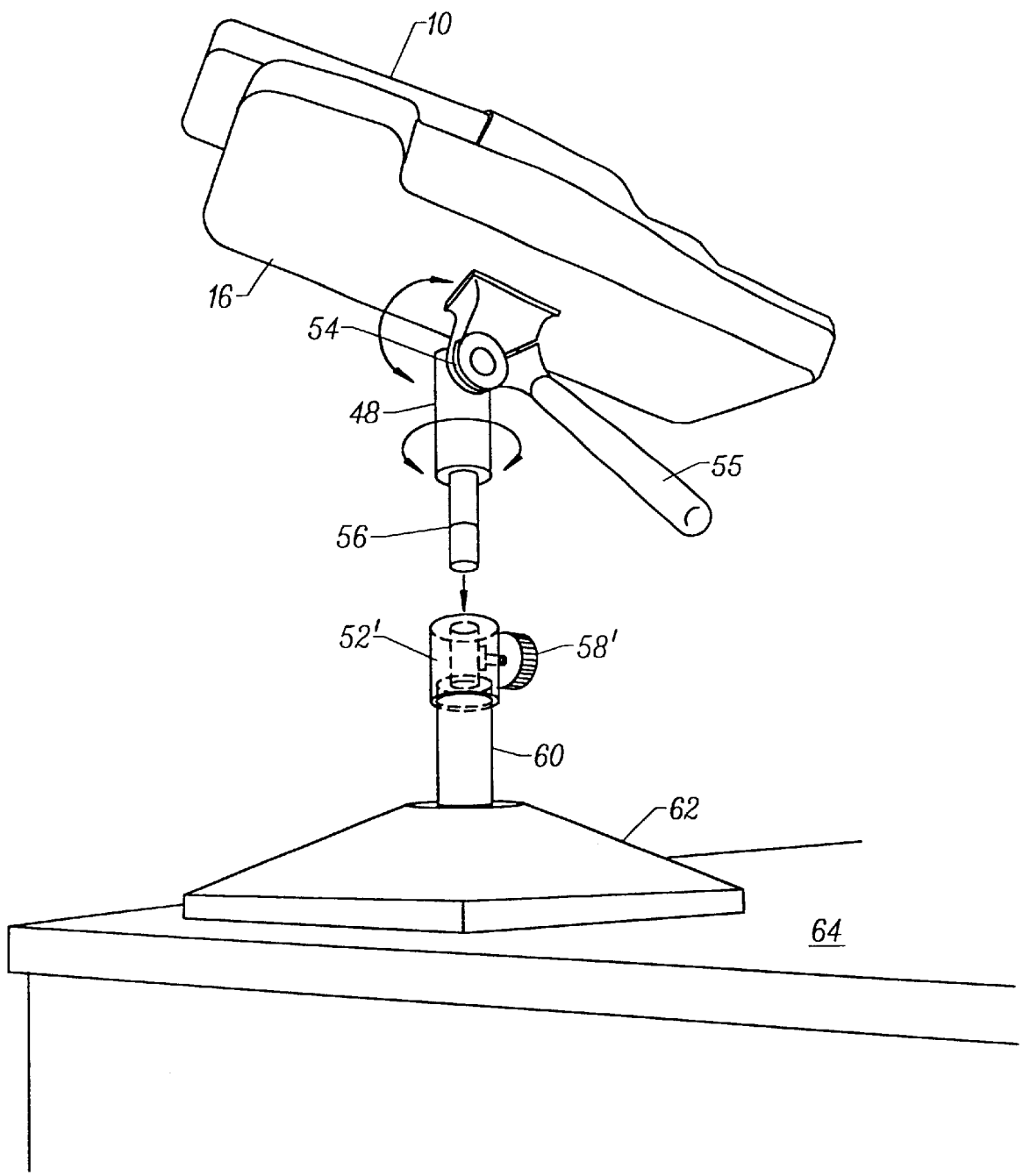
FIG. 4 is an exploded perspective view illustrating a first portion of the vertical support mating with a second portion of a second vertical support for desk use, for example.

Referring to FIG. 4, console 10, sleeve 16, and upper portion 48 of the vertical support can be removed from the moveable docking stand of FIG. 1 and placed on a second immobile base 62. Base 62 supports a lower vertical support 60 with a coupler 52' and thumb screw 58' receiving projection 56 from the upper vertical support 48. This embodiment of the invention is suitable for use on a desk 64, for example.

Figure 5:
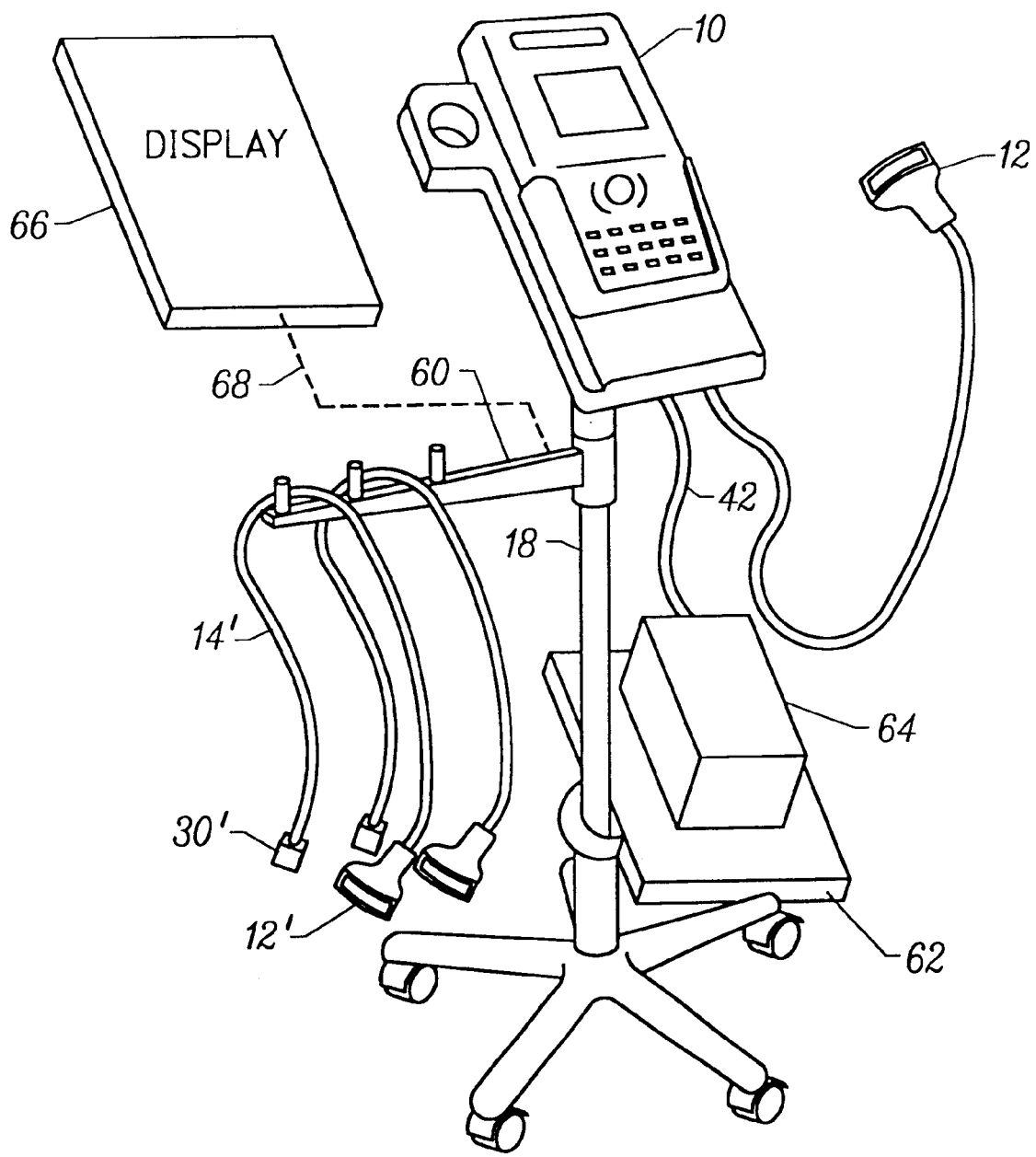
FIG. 5 is a perspective view illustrating a support arm for scanheads and a platform for a recorder in accordance with embodiments of the invention.

In practice, it is often desirable to have specific scanheads which are designed and programmed for specific applications such as gynecology, urology, and prostrate examinations for example. As shown in FIG. 5, an arm 60 is attached to the vertical support 18 for receiving a plurality of scanheads 12', cables 14', and connectors 30'. Further, each scanhead and connector can include special purpose software associated therewith for specific applications so that module 10 need not be programmed for all specific applications. A platform 62 can be attached to vertical support 18 for supporting a recorder 64 or communication unit, for example, to which the video signals from console 10 are connected through cable 42. Additionally, a flat panel display 66 can be supported by attachment 68 to vertical support 18 so that an operator can have a larger picture of the ultrasound image.

Figure 6:
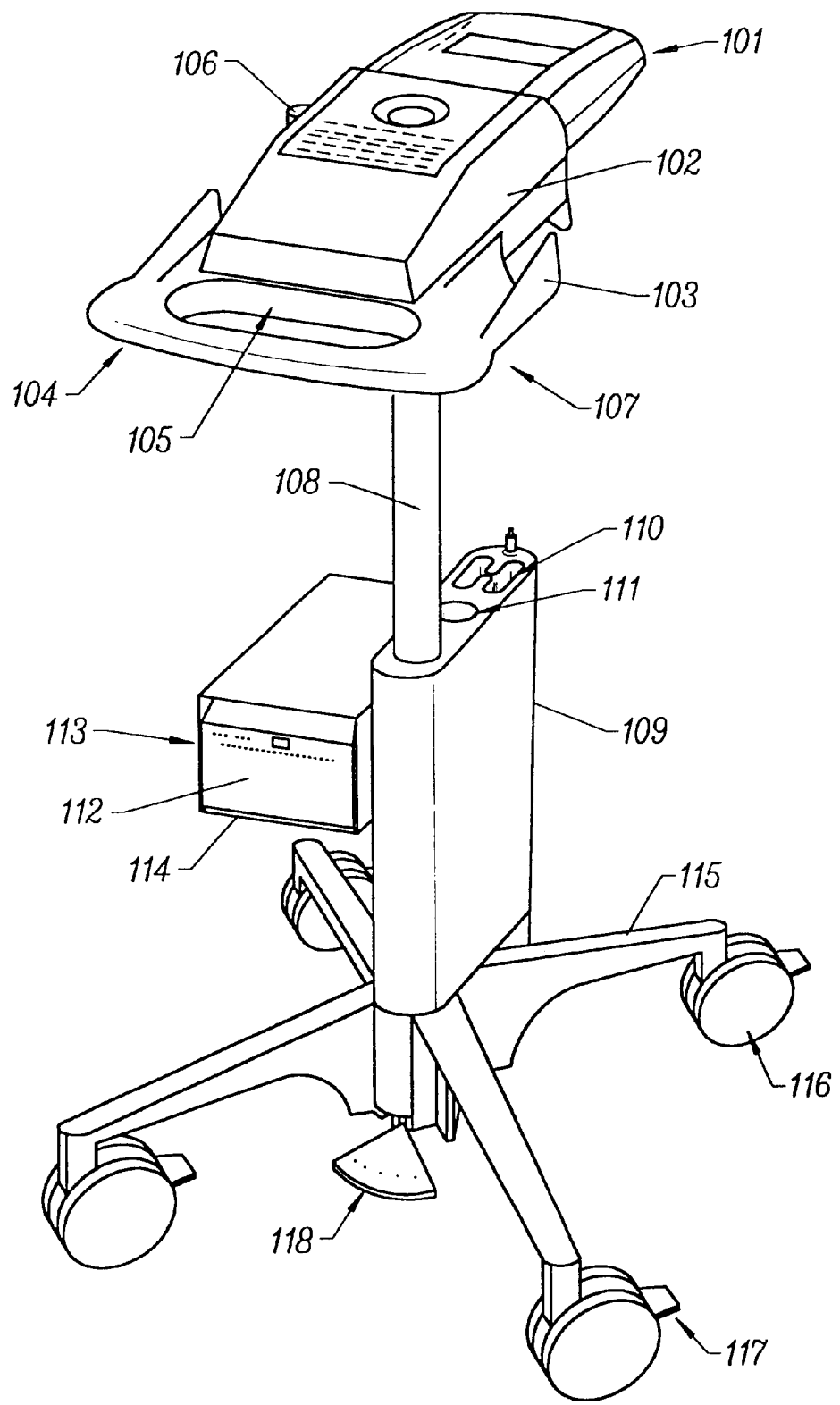
FIG. 6 is a perspective view of another embodiment of the invention.

FIG. 6 is an assembly drawing of another embodiment of the mobile stand illustrating its major features. Portable scanning unit 101 is supported by receiver assembly 102, which includes a positive locking mechanism to secure the device during use. A security lock may be added to prevent theft of the scanning unit. Note that the controls of the scanning unit are exposed, as is the transducer connector on the rear of the unit, thus allowing full functionality of the scanner while supported by the receiver assembly.

Transducer holder features 103 are provided on both sides of receiver assembly 102 to allow convenient storage of transducers on the stand. An additional support feature 106 is provided on one side to support long transducers such as an intervaginal transducer. The transducer holder features 103 incorporate a grip made of a soft material (e.g. rubber) to secure the transducer.

The receiver assembly 102 is mounted on a tilt and swivel head 10 that allows rotation and inclination of the assembly and the scanner unit. The receiver assembly 102 incorporates a handle 104 which allows convenient repositioning of the assembly and movement of the entire stand. The handle 104 is also designed so that a standard 8-oz. bottle of acoustic coupling gel which is used in ultrasound examinations can lay on its side in the handle opening.

The entire receiver assembly 102 and tilt/swivel mechanism 107 is mounted on support tube 108, which may be raised or lowered by applying pressure to pedal 118 which allows tube 108 to move up and down in a controlled manner. A gas piston assembly mounted in base wing 109 enables smooth, controlled motion. Base wing 109 also incorporates depression 111 suitable for storing a standard 8-oz. bottle of acoustic coupling gel, and depressions 110 suitable for holding the connector associated with an ultrasound transducer. Base wing 109 also incorporates mounting tracks to support accessory shelf 114. In this drawing, accessory shelf 114 is shown supporting a video printer 112 and top cover 113. Shelves may be used to support a variety of equipment including video recorders, image archive devices, and miscellaneous accessories.

The entire assembly is mounted on mobile base 115 which incorporates at least three wheels 116. At least two of these wheels may be locked to prevent motion of the stand, in this case via locking levers 117.

There has been described a mobile ultrasound diagnostic instrument and docking stand which is flexible in facilitating use of the instrument in a clinical environment either as a mobile unit for movement on the floor or as an immobile unit for positioning on a desk. While the invention has been described with reference to specific embodiments, the description is illustrative of the invention and is not to be construed as limiting the invention. For example, the vertical support for the docking stand can be provided with vertical flexibility and use by extending the vertical upper portion either inside the lower portion as described or by supporting the upper portion with clamps attached to the outside of the lower portion. Thus various modifications and applications may occur to those skilled in the art without departing from the true spirit and scope of the invention as defined by the appended claims.

What is claimed is:

1. A mobile ultrasound diagnostic instrument comprising:
   a) an ultrasound console including electronics for driving a transducer array and processing reflected ultrasound waves, a signal connector for input and output of signals or reception of video signals for an auxiliary display, and a visual display for processed ultrasound waves, and
   b) a docking stand including
      1) a sleeve for slidably receiving the console of the instrument, the sleeve configured to expose the visual display and manual control on the console, and having a signal connector for mating with said connector of the console,
      2) a vertical support for positioning the sleeve in a raised position, and
      3) a base for the vertical support.

2. The mobile ultrasound diagnostic instrument as defined by claim 1 wherein the console comprises a personal computer.

3. The mobile ultrasound diagnostic instrument as defined by claim 1 wherein said sleeve includes a power connector for mating with a power connector of the console for operating the console and for charging batteries in the console.

4. The mobile ultrasound diagnostic instrument as defined by claim 1 wherein said sleeve includes a power connector for mating with a power connector of the console for operating the console and for charging batteries in the console.

5. The mobile ultrasound diagnostic instrument as defined by claim 1 wherein said sleeve is attached to the vertical support by a motion joint whereby the sleeve can be rotated and/or tilted during use.

6. The mobile ultrasound diagnostic instrument as defined by claim 5 wherein the vertical supported is extendible to vary the height of the sleeve.

7. The mobile ultrasound diagnostic instrument as defined by claim 5 wherein the vertical support includes a coupler for joining a first portion of the vertical support attached to the sleeve and a second portion of the vertical support attached to the base, the first portion being removable from the second portion and attachable to a second vertical support.

8. The mobile ultrasound diagnostic instrument as defined by claim 7 wherein the base for the vertical support includes wheels for moving the docking stand.

9. The mobile ultrasound diagnostic instrument as defined by claim 8 wherein the second vertical support includes an immobile base.

10. The mobile ultrasound diagnostic instrument as defined by claim 5 and further including an arm attached to the vertical support and configured to receive a plurality of ultrasound transducer scanners and cables for use in interconnecting scanners and console.

11. The mobile ultrasound diagnostic instrument as defined by claim 10 and further including a shelf attached to the vertical support for supporting a device such as a recorder or communication unit.

12. The mobile diagnostic instrument as defined by claim 1 and further including a transducer scanhead and a cable connecting the scanhead to the console.

13. The mobile diagnostic instrument as defined by claim 1 and further including a display mounted to the stand.

14. The mobile diagnostic instrument as defined by claim 1 wherein the stand further includes controls for the transducer array.

* * * * *